(12) United States Patent
Vining et al.

(10) Patent No.: US 8,320,651 B2
(45) Date of Patent: *Nov. 27, 2012

(54) IMAGE REPORTING METHOD AND SYSTEM

(75) Inventors: David J. Vining, Winston-Salem, NC (US); Yaorong Ge, Winston-Salem, NC (US); David K. Ahn, Winston-Salem, NC (US); David R. Stelts, Rock Hill, SC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/198,884

(22) Filed: Aug. 5, 2011

(65) Prior Publication Data

US 2012/0033871 A1 Feb. 9, 2012

Related U.S. Application Data

(63) Continuation of application No. 12/947,232, filed on Nov. 16, 2010, now Pat. No. 7,995,823, which is a continuation of application No. 11/929,265, filed on Oct. 30, 2007, now Pat. No. 7,835,560, which is a continuation of application No. 10/931,477, filed on Aug. 31, 2004, now Pat. No. 7,289,651, which is a continuation of application No. 09/990,090, filed on Nov. 21, 2001, now Pat. No. 6,785,410, which is a continuation-in-part of application No. 09/635,515, filed on Aug. 9, 2000, now Pat. No. 6,819,785.

(60) Provisional application No. 60/147,914, filed on Aug. 9, 1999.

(51) Int. Cl.
*G06K 9/00* (2006.01)

(52) U.S. Cl. ...................................................... 382/128

(58) Field of Classification Search .......... 382/128–134; 128/922; 600/300; 705/2; 707/104.1
See application file for complete search history.

(56) References Cited

U.S. PATENT DOCUMENTS 4,315,309 A 2/1982 Coli
(Continued)

FOREIGN PATENT DOCUMENTS

CN 1239253 A 12/1999
(Continued)

OTHER PUBLICATIONS

"The ACR Breast Imaging Reporting and Data System (BI-RADS®)", Copyright ® 1994-2002 American College of Radiology, Revised Jun. 1, 2000.

(Continued)

*Primary Examiner* — Jose Couso
(74) *Attorney, Agent, or Firm* — Niels Haun; Dann, Dorfman, Herrell & Skillman, P.C.

(57) ABSTRACT

A method and system are provided to report the findings of an expert's analysis of image data. The method and system are based on a reporting system that forms the basis of an image management system that can efficiently and systematically generate image reports, facilitate data entry into searchable databases for data mining, and expedite billing and collections for the expert's services. The expert identifies a significant finding on an image and attaches a location:description code to the location of that finding in order to create a significant finding and an entry into a database. Further descriptions of that finding, such as dimensional measurements, may be automatically appended to the finding as secondary attributes. After the evaluation, the system sorts the findings in the database and presents the findings by prioritized categories. The expert edits and approves a multimedia report which may be delivered by electronic means to an end-user.

5 Claims, 15 Drawing Sheets

U.S. PATENT DOCUMENTS

| | | |
|---|---|---|
| 5,115,501 A | 5/1992 | Kerr |
| 5,148,366 A | 9/1992 | Buchanan et al. |
| 5,235,510 A | 8/1993 | Yamada et al. |
| 5,267,155 A | 11/1993 | Buchanan et al. |
| 5,437,278 A | 8/1995 | Wilk |
| 5,452,416 A | 9/1995 | Hilton et al. |
| 5,463,548 A | 10/1995 | Asada et al. |
| 5,506,984 A | 4/1996 | Miller |
| 5,528,492 A | 6/1996 | Fukushima |
| 5,542,003 A | 7/1996 | Wofford |
| 5,581,460 A | 12/1996 | Kotake et al. |
| 5,587,833 A | 12/1996 | Kamentsky |
| 5,666,400 A | 9/1997 | McAllister et al. |
| 5,704,367 A | 1/1998 | Ishikawa et al. |
| 5,715,449 A | 2/1998 | Peters, Jr. et al. |
| 5,740,267 A | 4/1998 | Echerer et al. |
| 5,762,608 A | 6/1998 | Warne et al. |
| 5,779,634 A | 7/1998 | Ema et al. |
| 5,782,762 A | 7/1998 | Vining et al. |
| 5,793,969 A | 8/1998 | Kamentsky et al. |
| 5,807,256 A | 9/1998 | Taguchi et al. |
| 5,825,908 A | 10/1998 | Pieper et al. |
| 5,878,746 A | 3/1999 | Lemelson et al. |
| 5,920,317 A | 7/1999 | McDonald |
| 5,920,319 A | 7/1999 | Vining |
| 5,986,662 A | 11/1999 | Argiro et al. |
| 6,014,581 A | 1/2000 | Whayne et al. |
| 6,032,678 A | 3/2000 | Rottem |
| 6,058,322 A | 5/2000 | Nishikawa et al. |
| 6,117,073 A | 9/2000 | Jones et al. |
| 6,252,979 B1 | 6/2001 | Lee et al. |
| 6,282,305 B1 | 8/2001 | Huo et al. |
| 6,292,577 B1 | 9/2001 | Takahashi |
| 6,317,617 B1 | 11/2001 | Gilhuijs et al. |
| 6,366,683 B1 | 4/2002 | Langlotz |
| 6,415,048 B1 | 7/2002 | Schneider |
| 6,490,370 B1 | 12/2002 | Krasinski et al. |
| 6,551,243 B2 | 4/2003 | Bocionek et al. |
| 6,630,937 B2 | 10/2003 | Kallergi et al. |
| 6,785,410 B2 | 8/2004 | Vining et al. |
| 6,819,785 B1 | 11/2004 | Vining et al. |
| 6,898,302 B1 | 5/2005 | Brummer |
| 7,289,651 B2 | 10/2007 | Vining et al. |
| 7,835,560 B2 * | 11/2010 | Vining et al. .................. 382/128 |
| 7,995,823 B2 | 8/2011 | Vining et al. |
| 2001/0025279 A1 | 9/2001 | Krulak et al. |
| 2002/0004798 A1 | 1/2002 | Babula et al. |

FOREIGN PATENT DOCUMENTS

| | | |
|---|---|---|
| CN | 625584 | 5/2010 |
| JP | 4-333971 | 11/1992 |
| JP | 10-014864 | 1/1998 |
| JP | 10-063752 | 3/1998 |
| JP | 2001-187044 | 7/2001 |
| JP | 510326 | 4/2005 |
| WO | 9816903 | 4/1988 |
| WO | 99/66394 | 12/1999 |
| WO | 01/11548 A1 | 2/2001 |
| WO | 03046810 A1 | 6/2003 |

OTHER PUBLICATIONS

Bell, D.S.., et al., "Evaluation of UltraSTAR: Performance of a Collaborative Structured Data Entry System", 1994, AMIA, Inc.; Symposium Supplement, pp. 216-222.

Chronaki, C. et al., "I2Cnet Medical Image Annotation Service", Medical Informatics, Online!, vol. 22, No. 4, 1997, pp. 337-347.

Campbell, K.E., et al., "A Computer-Based Tool for Generation of Progress Notes", 1993; Symposium Supplement 284-288.

Dockray, Karl T., "Solo Practice Management: Value of a Computerized Reporting System", Computers in Radiology, JR 1994, 162:1439-1441.

Friedman, C., et al., "A Schema for Representing Medical Language Applied to Clinical Radiology", Journal of the American Medical Informatics Assoc., vol. 1, No. 3, May/Jun. 1994, 1:233-248.

Hundt, W., et al., "A Computer-based reporting system in radiology of the chest", European Radiology, 8, 1002-1008 (1998), Springer-Verlag 1998, 8:1002-1008.

Brolin, "MEDELA: An Electronic Data-Processing System for Radiological Reporting", Radiology 103:249-255, May 1972.

Barnhard, et al., "Computer Autocoding, Selecting and Correlating of Radiologic Diagnostic Cases", Apr. 1966, pp. 854-863.

Bell, et al., "Experiments in Concept Modeling for Radiographic Image Reports", J Am Med Informatics Assoc., 1994, 1:249-262.

Jost, "Radiology Reporting", Radiologic Clinics of North America—vol. 24, No. 1, Mar. 1986.

Bluemke, et al., "An Automated Radiology Reporting System That Uses HyperCard", Computers in Radiology, AJR 1993; 160:185-187 0361-803X/93/1601-0185 American Roentgen Ray Society, Jul. 23, 1992.

Dietrich, "Knowledge-Based Computer-Assisted Diagnosis of Chest Radiographs", Radiologic Clinics of North America—vol. XVI, No. 3, Dec. 1978.

eDict Systems, Inc., www.edictation.com printed website on Nov. 21, 2000.

Kahn, Jr., et al., "Structured Entry of Radiology Reports Using World Wide Web Technology", RadioGraphics 1996; 16:683-691, RSNA, 1996.

Leeming, et al., "Advances in Radiologic Reporting with Computerized Language Information Processing", Radiology 133:349-353, Nov. 1979.

Langlotz, G.P., MD, PhD, "A Graphical Speech-guided Structured Reporting System", 1999 Scientific Program Radiological Society of North America 56th Scientific Assembly and Annual Meeting, Supplement Nov. 1999, v213(p), p. 578.

Langlotz, "Enhancing the Expressiveness of Structured Reporting Systems", Journal of Digital Imaging, vol. 13, No. 2, Suppl. 1 (May 2000): pp. 49-53.

Mani, et al., "A Computer-Assisted Radiologic Reporting System", Radiology 108:587-596, Sep. 1973.

Pendergrass, et al., "An On-Line Computer Facility for Systematized Input of Radiology Reports", Radiology 1969; 92:709-713.

Poon, A.D., et al., "PEN-Ivory: The Design and Evaluation of a Pen-Based Computer System for Structured Data Entry", Stanford University School of Medicine, Journal of the American Medical Informatics Assoc., 1994; (Symposium Supplement) 447-451.

Puerta, A., et al., "Towards a General Computational Framework for Model-Based Interface Development Systems", Stanford University, Proceeding of the International Conference on Intelligent User Interface Design, Calif. 1999.

Sahoo, et al., "A Survey of Thresholding Techniques", Computer Vision, Graphics, and Image Processing (Feb. 1988), No. 2, Duluth, MN, USA, pp. 233-260.

Vining, et al., "Freeflight", Digestive Disease Week and the 100th Annual Meeting of the Gastroenterological Assoc., May 16-19, 1999, Orlando, FL, program v116, n4, p. 2.

Vining, et al., "New Paradigm for Virtual Colonoscopy Processing and Reporting", and "New Paradigm for Digital Image Reporting", 1999 Scientific Program Radiological Society of North America 85th Scientific Assembly and Annual Meeting, Supplement Nov. 1999, v213(p), p. 577 and p. 579.

Wheeler, et al., "The John Hopkins Radiology Reporting System", Radiology 119:315-319, May 1976.

Bidgood, W., Jr., "Clinical Importance of the DICOM Structured Reporting Standard", International Journal of Cardiac Imaging 14: 307-315, 1998.

Bidgood, W., Jr., "Documenting the Information Content of Images", Proc AMIA Annual Fall Symp., 1997; 424-8.

Noboru Maki, Image Processing Expanding Particularly in the Medical and the Mapping Fields, Nikkei Computer Graphics, Jan. 1990, p. 63 (English translation: Transmittal No. 574154).

* cited by examiner

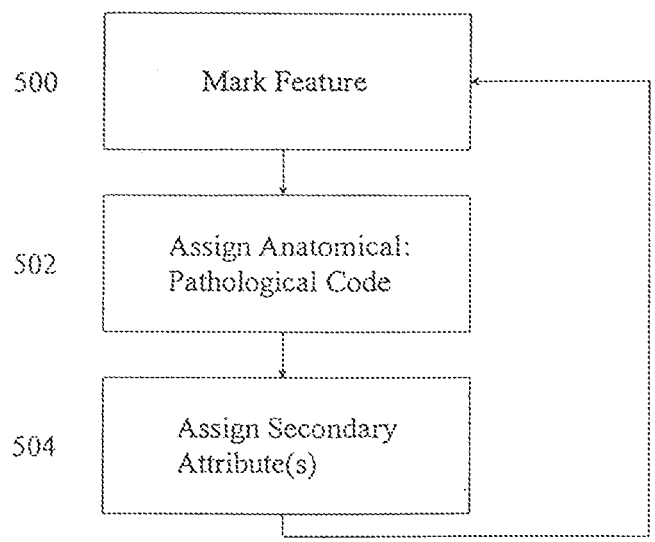
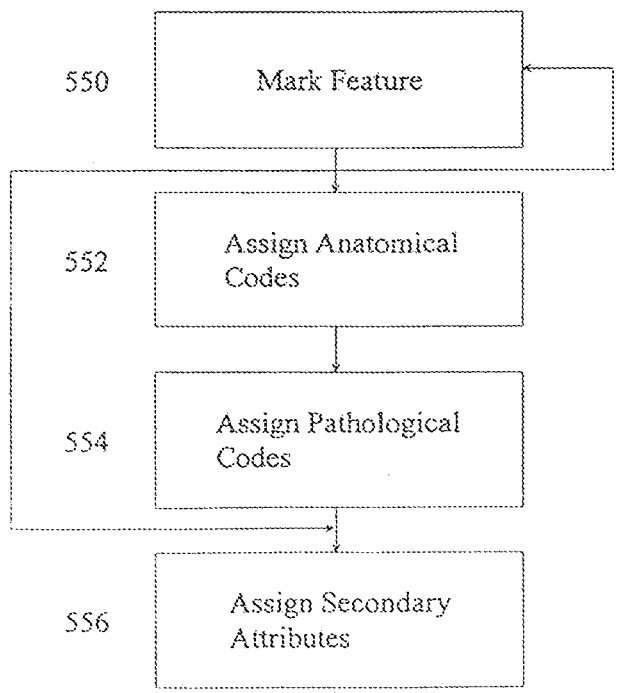

New Paradigm Report

Wake Forest University / Baptist Medical Center

| | | | |
|---|---|---|---|
| Patient Name: | DOE, JOHN | Radiologist: | VINING, DAVID |
| Patient ID: | 12345678 | Referring Physician: | WELBY, MARCUS |
| Requisition #: | 87654321 | | |
| Sex: | Male | Date of Exam: | 10/19/1998 |
| DOB: | 1/1/1942 | Date of Report: | 11/3/1998 |

Indication: Colon cancer screening (V76.49)

Patient Prep: Liquid diet, split-dose Fleets Phospho-soda, Gastroview, $CO_2$ insufflation.

Technique: Virtual colonoscopy protocol - CT abdomen (CPT 74150), CT pelvis (CPT 72192), 3D reconstruction (CPT 76375)

Findings

Lungs: Normal.

Liver: Normal.

Spleen: Normal.

Pancreas: Normal.

Gallbladder:

Finding 1: Gallbladder: calculi (ACR 762.81)
        *Exam:* 999, *Series:* 5, *Acquisition:* 1, *X, Y, Z:* -82.3, -36.3, -76.9

Features: *Status:* Recommend clinical correlation
        *Characteristics:* multiple gallstones
        *Size:* 8 mm
        *Voice:* [click for voice description]

Images:

Fig. 7A

Images: 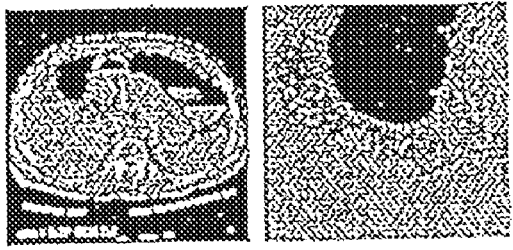

Adrenals: Normal.

Kidneys: Normal.

Colon:

Finding 1a: Colon, rectum: adenomatous polyp (ACR 757.3111)
Exam: 999, Series: 5, Acquisition: 1, X,Y,Z: 26.8, 19.2, -367.9

Features: Status: HIGH Priority - Requires surgical attention
Characteristics: polypoid, located on left wall, surrounded by fluid
Size: 10 mm
Voice: [click for voice description]

Images: 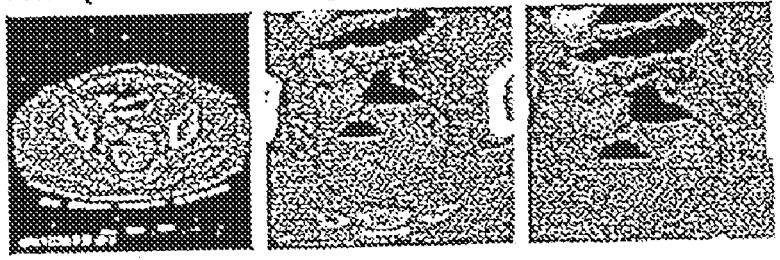

Finding 1b: Colon, rectum: adenomatous polyp (ACR 757.3111)
Exam: 999, Series: 5, Acquisition: 2, X,Y,Z: 337.1, 354.9, -161.3

Features: Status: HIGH Priority - Requires surgical attention
Characteristics: polypoid, located on left wall
Size: 10 mm
Voice: [click for voice description]

Images: 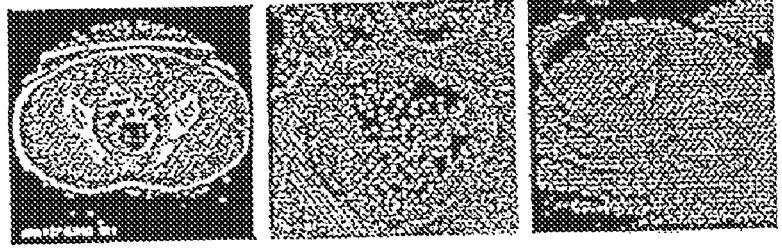

Fig. 7B

Skeleton:

Finding 1:    Lumbosacral spine: degenerative joint disorder (ACR 33.77)
                        Exam: 999, Series: 5, Acquisition: 1, X,Y,Z: -27.7, 38.2, -272.9
    Features:    Status: n/a
                        Characteristics: minimal hypertrophic changes
                        Size: n/a
                        Voice: [click for voice description]
    Images:

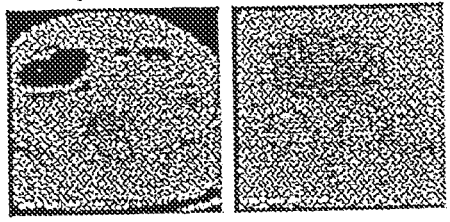

Misc:

Finding 1:    Abdominal aorta: atherosclerosis (ACR 981.721)
                        Exam: 999, Series: 5, Acquisition: 1, X,Y,Z: 9.1, -25.0, -177.9
    Features:    Status: n/a
                        Characteristics: minimal atherosclerosis
                        Size: n/a
                        Voice: [click for voice description]
    Images:

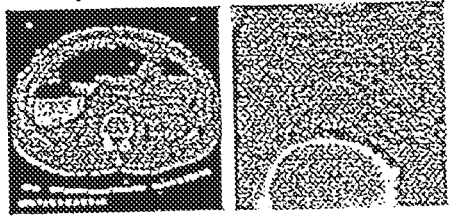

Fig. 7C

Original Anatomy Menu

Head
Neck
Chest
Abdomen
Pelvis
Upper Extremity
Lower Extremity

Fig. 8A

After Spleen Selection

Spleen
**************
Head
Neck
Chest
Abdomen
Pelvis
Upper Extremity
Lower Extremity

Fig. 8B

After Liver Selection

Liver
Spleen
**************
Head
Neck
Chest
Abdomen
Pelvis
Upper Extremity
Lower Extremity

Fig. 8C

Diverticulosis
Polyp
**************
Normal
Inflammation
Neoplasm
Trauma
Systemic
Functional
Other
Indeterminate Dx
Artifact

IMAGE REPORTING METHOD AND SYSTEM

RELATED APPLICATIONS

This application is a continuation of application Ser. No. 12/947,232, entitled "Image Reporting Method and System", filed on Nov. 16, 2010, and issued as U.S. Pat. No. 7,995,823, which in turn is a continuation of application Ser. No. 11/929,265, filed Oct. 30, 2007, now U.S. Pat. No. 7,835,560, which in turn is a continuation of application Ser. No. 10/931,477, filed Aug. 31, 2004, now U.S. Pat. No. 7,289,651, which in turn is a continuation of application Ser. No. 09/990,090, filed Nov. 21, 2001, now U.S. Pat. No. 6,785,410, which in turn is a continuation-in-part of application Ser. No. 09/635,515, filed Aug. 9, 2000, now U.S. Pat. No. 6,819,785, which in turn claims the benefit of priority to U.S. Provisional Application 60/147,914, filed on Aug. 9, 1999, the contents of which applications are incorporated herein by reference.

FIELD OF THE INVENTION

The present invention relates generally to an image reporting method and system and more particularly to a method and computer-implemented procedure for creating electronic, multimedia reports based on a new reporting paradigm.

BACKGROUND OF THE INVENTION

Image reporting as currently practiced suffers from a lack of standardization, consistency, accountability, and efficiency. A root cause of these problems is the manner in which reports are generated, beginning with the lack of a standardized report format, particularly in the medical field of radiology.

Radiologists generally review images of a body structure and dictate narrative descriptions of their image findings followed by summary statements. Clerical workers then transcribe the dictated statements and either print applicable reports or enter such information into a computerized radiology information system (RIS) and/or hospital information system (HIS). As a result, the content and format of radiology reports often vary greatly depending on the differing preferences and styles of individual radiologists. This inconsistency among the radiologists' reporting styles often hinders the correlation of the reported findings with the actual images by the recipients of the reports. Variability in the reporting styles also impedes on-going monitoring of specific findings from different examinations on the same patient, a task that is critical for patient care and time-consuming for radiologists. Further, traditional radiology reporting practices do not support data mining, a powerful tool which is useful in clinical trials, epidemiology studies, and outcomes analyses.

In addition, conventional reporting practices often provide no mechanism to allow the radiologist to account for the effective communication of critical report information to the recipient. Frequently, radiologists mistakenly assume that when a report is approved and sent to a referring medical professional, their responsibility ends. To the contrary, radiologists are often held accountable for ensuring that proper action is taken on significant findings and are held liable for malpractice when proper action is not taken.

Clinicians are the typical end-users of reports from radiologists. A major complaint of such clinicians against radiologists and their reporting practices involves point of service. This problem is illustrated by the following scenario: a patient receives emergency room x-rays for an injury during the night; a radiologist interprets the x-ray images the next morning; and, following transcription, a report is finally delivered to the emergency room physician, but typically only after the patient has been treated and released. Clinicians are now demanding that radiologists issue reports immediately after an imaging study has been performed.

Hence, there is a pressing need to provide a reporting system which offers a standardized report format, enables consistency among reports, accounts for effective information flow, provides for quick turnaround of information to the end-user, provides for on-going tracking of previous findings, and supports data mining for public health statistics. In addition, these needs extend beyond the field of radiology, and include other medical fields such as pathology, histology, cardiology, dermatology, as well as other image analysis fields such as satellite imagery and photography.

SUMMARY OF THE INVENTION

The present invention relates to a new reporting method and system for reporting the findings of an expert's analysis of image data and, more specifically, to a computer system and computer-implemented method for reporting an expert's findings relative to an analysis of image data. The method and system are based on a new structured reporting paradigm. The paradigm forms the basis of a radiology practice management system that can efficiently and systematically generate radiology reports, facilitate data entry into searchable databases, track findings, support clinical trials and outcomes analyses, and expedite hospital billing and collections. One fundamental aspect of this paradigm is that a user, e.g. an expert-radiologist, identifies a significant feature on an image and attaches a location:description code. The location:description code can describe what or who is present in the image, when the image was taken, where the image was taken, and how the image was taken. For example, in the case of consumer digital photography, the user can attach a location:description code to a digital photograph in order to create a finding that indicates "Aunt Minnie: Vacationing at the beach", or in the case of radiology can attach an anatomical:pathological code to the location of an image feature to create a diagnostic finding. In the case of medical imaging, the anatomical:pathological code includes the anatomical location followed by a pathological description.

Optionally, further attributes of that finding, such as follow-up treatment or diagnosis recommendations, a priority descriptor, dimensional measurements (e.g., length, area, and volume), audio descriptions, 3D rendered snapshots, etc., may be automatically appended to the diagnostic finding as secondary attributes of the diagnostic finding. All of this information is automatically captured in an intuitive workflow scheme transparent to the expert, and stored in a database. The expert may continue to identify additional diagnostically significant features and create diagnostic findings in any order.

At the end of the expert's evaluation of the image(s), the system sorts the diagnostic findings by selected or predetermined categories. In a medical field, these predetermined categories may be anatomical categories. The diagnostic findings are further prioritized by the severity of the diagnosis, e.g., the priority descriptor, in order to alert the report recipient, such as a clinician. In addition, the system may alert the expert and display a summary of significant prior findings, including trend data, relating to the present image analysis. The expert can edit and approve a multimedia report, which may be delivered to an Internet server for immediate access, sent to a database, sent by automated voice, fax, e-mail, or wireless personal digital assistant (PDA) (e.g. Palm™ handheld) to the clinician, or any combination thereof. The radiologist can sign the report by electronic or voice signature. The final report presentation may be further customized to satisfy the needs of the clinician.

The reporting system of the present invention is applicable to several other image-based fields including, without limitation, pathology, histology, cardiology, dermatology, satellite imagery, and photography.

BRIEF DESCRIPTION OF THE DRAWINGS

The foregoing summary and the following detailed description of the preferred embodiments of the present invention will be best understood when read in conjunction with the appended drawings, in which:

FIGS. 5A and 5B illustrate the steps of annotating findings;

FIG. 6 illustrates the user-interface of the present invention in which

FIGS. 7A-7C illustrate a selected report of the present invention;

FIGS. 8A-8D illustrate anatomy and pathology hot menus;

FIGS. 9A-9C illustrate the display of significant prior findings; and

DETAILED DESCRIPTION OF THE INVENTION

Figure 1:
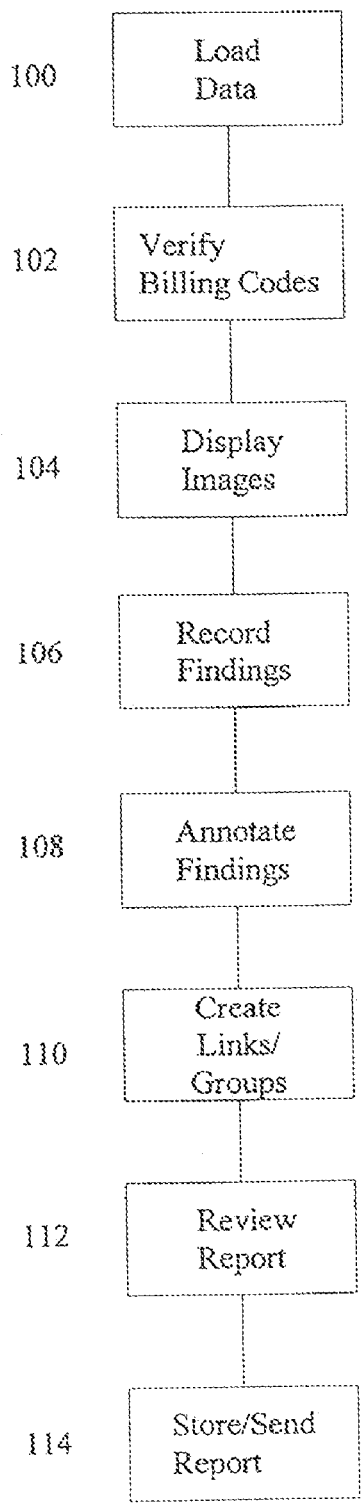
FIG. 1 illustrates a flowchart representing a general method in accordance with the present invention for creating an image report.
Figure 2:
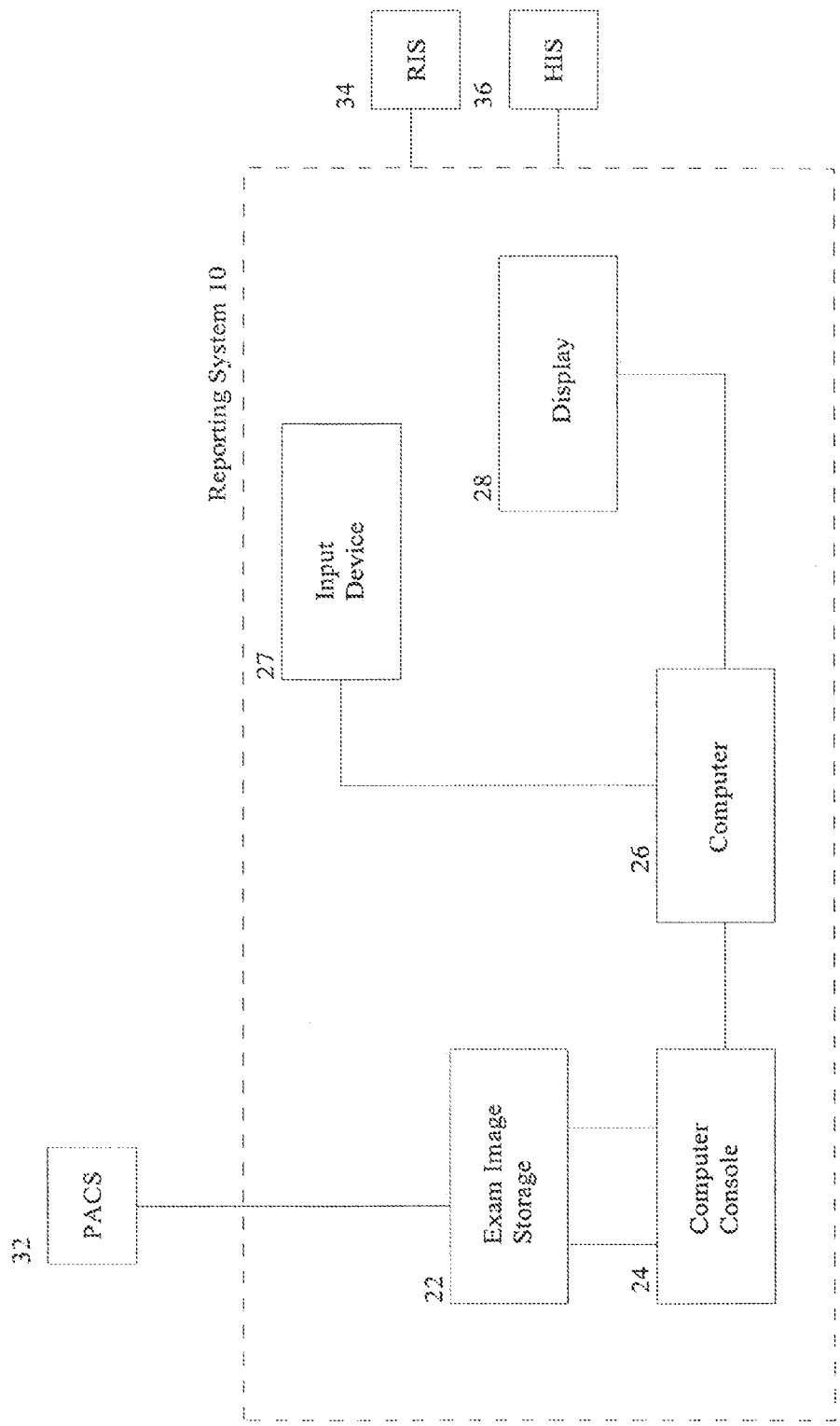
FIG. 2 illustrates a block diagram of a computer system used in the computer-implemented method of the present invention.

A method and system are provided for generating and communicating reports containing an expert's analysis of image data as generally depicted in FIGS. 1 and 2. In addition, a computer-implemented method and a computer system function to create a database of the expert's findings from which a report is generated and from which data mining and other analyses may be conducted. The database can be a computer searchable database and may be a relational computer database.

The method and system of the present invention are applicable to any field which relates to a user's analysis of images. In particular, however, the method and system of the present invention are well-suited to image analysis found in medical applications. As such, the method and system of the present invention are illustrated in the accompanying figures and description in terms of the medical field of radiology.

The method and system are particularly well-suited to the analysis of digital images. However, the method and system may also be adapted for use with analog images such as conventional x-ray films and conventional photographs. For example, the system can utilize a digital camera to load a digital representation of an analog image into computer memory for further processing.

The computerized reporting system 10 is designed to interface with existing information systems such as a Hospital Information System (HIS) 36, a Radiology Information System (RIS) 34, and a Picture Archiving and Communication System (PACS) 32, and to conform to certain standards including but not limited to the Digital Imaging and Communications in Medicine (DICOM) standard, DICOM Structured Reporting (SR) standard, or the Radiological Society of North America's Integrating the Healthcare Enterprise (IHE) initiative. The reporting system 10 includes an examination image storage 22, a computer console 24, a computer 26, display(s) 28, and an input device 27. For illustration purposes the input device 27 is a three-button computer mouse, where the left and middle-mouse buttons (LMB, MMB) are used, for example, to manipulate image data, and the right-mouse button (RMB) is used, for example, to identify a new diagnostically significant feature and to start a database recording process. Other known input devices including LCD graphics tablets and touch-screens may be used as well as other custom devices. For example, an intelligent view box and digital camera device can be used with conventional x-rays.

Bidirectional communication between the reporting system 10 and the information systems 32, 34, 36 allows the reporting system 10 to retrieve data from the information systems 32, 34, 36 and to update information in these systems to provide the desired report generated by the reporting system 10. For example, the reporting system 10 may download image data corresponding to radiological examinations of patients from the PACS 32, and additional information including but not limited to patient demographics, billing information, laboratory data, and pathology reports from the HIS 36. The PACS 32 stores information according to existing standards such as (DICOM). The data from the PACS 32 is stored in the examination image storage 22 where it can be accessed via the computer console 24 and computer 26 for display on the display 28. Alternatively, the reporting system 10 can directly access the PACS images without the need for an intermediate storage device, such as image storage 22. Additionally, the reporting system 10 may be linked to communication systems such as the Internet, e-mail systems, fax, telephone, wireless communications systems such as pagers and cellphones, wireless PDA's and other communication systems.

Figure 3:
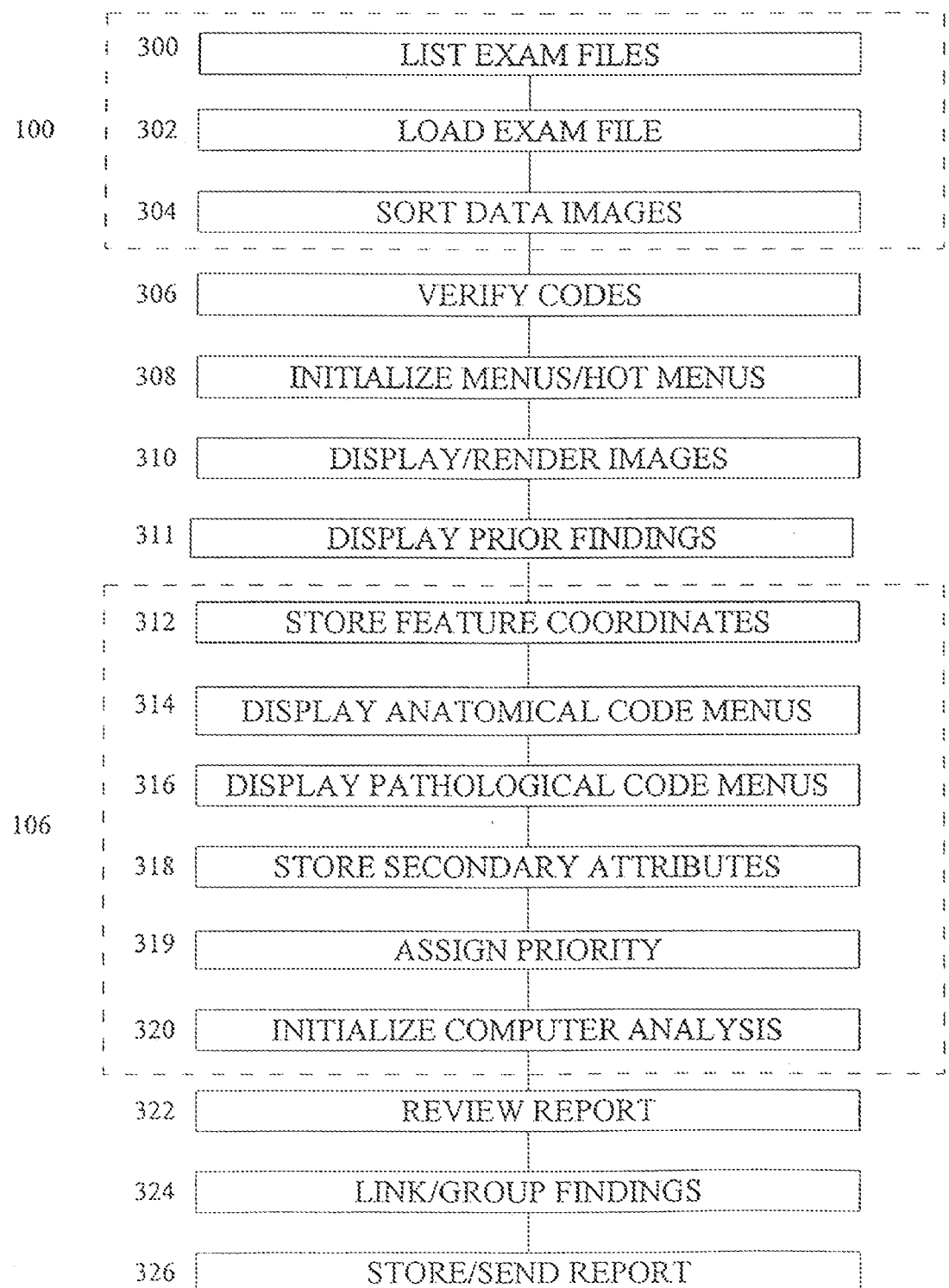
FIG. 3 illustrates a flowchart representing the steps of the process for creating an image report.

Referring now to FIGS. 1 and 3 which illustrate the general method and detailed process steps of the present invention, respectively, preparation of a report begins with the loading of patient data, including but not limited to billing, demographics, laboratory data, pathology reports, and image data, step 100. A file loader from computer 26 searches the examination storage 22 for examination data files available for analysis and displays the corresponding names of patients in a user-interface at step 300. Upon selection of a particular patient by the radiologist, the file loader displays all of the associated unread examination files for that patient. The radiologist selects a particular examination file, and the file loader loads the corresponding data into computer memory at step 302. The file loader searches through the image data in the selected examination and organizes the images by DICOM series (or any additional subdivisions), at step 304, prior to display in 2D, and optional 3D, viewers.

The file loader also displays the Current Procedural Terminology (CPT) and International Classification of Diseases (ICD) codes assigned to the selected examination and determines if they correlate at steps 102 and 306. (CPT codes describe the type of radiologic examination, and ICD codes indicate the reasons for performing a particular examination.) Proper matching of these codes are essential for reimbursement by health care insurers. The file loader compares the ICD and CPT codes and displays an alert if the codes are incompatible. The radiologist verifies the codes and enters any necessary changes. Correct assignment of these codes at the beginning of an examination is effected by the reporting system 10 to intelligently guide the presentation of diagnostic code menus during the annotation process described below. Prior to the review process, an anatomical-location menu and a pathology-description menu are initialized using the CPT codes at step 308. For example, if the CPT code describes that the examination encompasses a computed tomography (CT) scan of a patient's abdomen, then the anatomical-location menu may present specific elements such as "liver, spleen, pancreas, kidneys, etc" and not necessarily anatomical locations corresponding to head and extremity body structures. Of course, the system allows a user to access a "master index" (or dictionary) of all anatomical and pathological codes. In addition, the CPT codes guide default settings for window/level (W/L) settings, 3D opacity map settings, and report organization/layout. Likewise, a series menu is initialized to list all of the DICOM series available in the selected examination file at step 308. In addition, the file loader retrieves existing "new paradigm" reports, i.e., those created using the present invention, from the patient's previous examinations and makes them available for review during the current study.

One problem that can be encountered in the use of the anatomical-location and pathology-description menus is that the radiologist can be presented with so many menu choices that an inordinate amount of time is required to make a menu selection. Such a large number of choices may unnecessarily increase the cost of creating a report and may create user fatigue and increased risk for a repetitive stress injury. Accordingly, it would be desirable to limit the choices presented to the radiologist. The system of the present invention addresses such problems through the use of "hot menus."

A "hot menu" may utilize information from the CPT codes, ICD codes existing reports which have been loaded at step 308, and/or user trends determined by data mining analysis of the user's prior reports to tailor the menus, such as the anatomical-location menu and pathology-description menu. For example, the data contained in the current report and/or in any previous reports can be used to reorder the presentation of menu choices, so that the selections used most recently and/or most frequently are presented earlier in the menus. For example, if the most recently selected anatomy was "spleen", then "spleen" would appear at the top of the anatomical-location menu in a hot menu section, as shown in FIGS. 8A-8C. A separator, such as a row of asterisks or a line, could be placed below menu choices that are moved to a higher level of the menu to differentiate these choices from the choices located at their standard positions within the menu. Similarly, the most recently or most frequently selected pathology-descriptions, as determined from pre-existing reports, may be presented as hot menu selections at the top of the pathology-description menu, as shown in FIG. 8D. As an alternative to a simultaneous presentation of hot menu selections with ordinary menu items, the menu may show only the recent and/or frequent selections followed by a click-able menu entry which expands to show the standard options when the user clicks on that entry.

One rationale for this approach is that an organ is usually evaluated in its entirety at any given time. If the right kidney contains multiple cysts, then the user may want to click on several cysts in the right kidney in rapid succession. In such a case it would be very efficient to see kidney appear at the top of the anatomy menu and the term cyst appears at the top of the pathology menu. Likewise, it would be very efficient to see the term "right" appear as the default in the characteristic field.

In addition, the anatomical and pathological menu presentations may be modified by removing irrelevant choices from the anatomical-location menu or pathology-description menu. Data present in the loaded reports can be analyzed for certain information, such as the patient's sex, and the anatomical-location and/or pathology-description menus can be modified appropriately. For example, the anatomical-location menu associated with genitalia can be tailored to include only genitalia choices appropriate to the sex of the patient. As a further example, if a particular diagnostic procedure, as indicated by the CPT codes, is incapable of detecting a certain diagnosis, then menu choices associated with that diagnosis can be removed. Likewise, if information in the image data indicates that the image data relates to the brain, then menu choices associated with the neck, chest, abdomen, pelvis, and extremities need not be included.

Figure 6A:
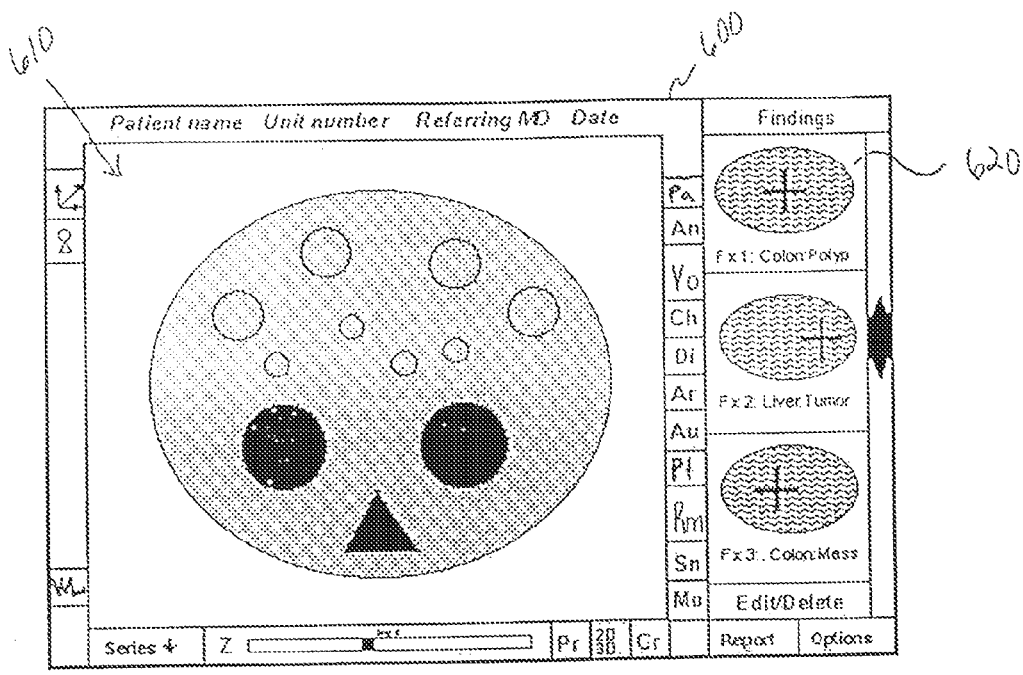
FIG. 6A shows a 2D viewer and FIG. 6B shows a 3D viewer.

After initialization of the menus, the first available image from the sorted images is displayed in a user-interface by a 2D viewer 610 as shown in FIG. 6A from which the radiologist may begin analysis of the first image, at steps 104 and 310. Alternately, the radiologist is free to select a different DICOM series for evaluation from the series menu. For example, a CT or MRI examination often consists of multiple series, whereas a chest x-ray may contain only one series. Two or more series may also be displayed simultaneously (e.g., supine and prone series of a virtual colonoscopy study). When a single window display is employed, a "previous" button allows the radiologist to toggle between the two most recently viewed series. A window/level menu, W/L, is available as part of the user-interface which lists preset window and level settings (i.e., grayscale settings) for the 2D viewer. The preset settings can be specified in an options menu or modified using window/level sliders.

The step of displaying and rendering images, step 310, includes altering the display of the images in response to commands from the radiologist. For example, the radiologist can pan through a number of images in the 2D viewer as the mouse is moved and the LMB is pressed, provided that more than one image is contained in the series. Similarly, the 2D viewer can translate (i.e., move) the image up/down and sideways when the mouse is moved and the MMB is pressed. The 2D viewer can also zoom the image display when the mouse is moved and the LMB and MMB are pressed simultaneously. An overview button is provided in the user-interface to re-center the image in case the scene is moved out of sight. However, re-centering may be unnecessary if the ability to move or zoom an image is restricted.

Figure 6B:
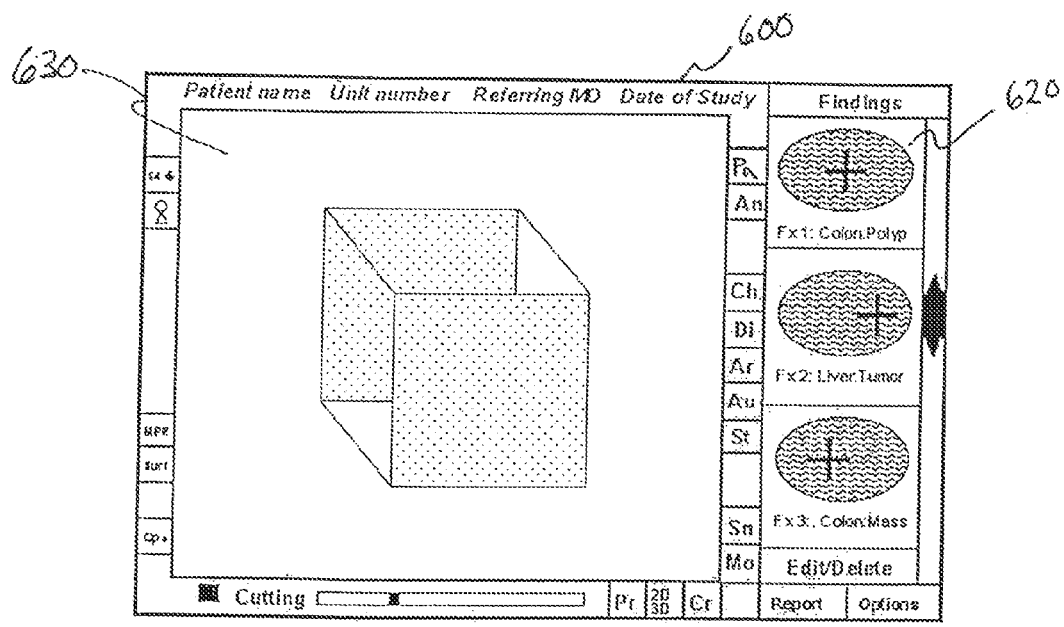

A 3D viewer is also provided in the user-interface, as shown in FIG. 6B to render images in step 310. A 2D/3D toggle button is also included in the user-interface to allow the radiologist to toggle between the 2D and 3D viewers at step 310. In the 3D viewer, the mouse operations are similar to those of the 2D viewer except that pressing the LMB while moving the mouse causes the 3D rendered scene to rotate in space. The LMB can also be used to control a "fly-through" mode as used in virtual endoscopy as disclosed in U.S. Pat. No. 5,782,762.

The 3D viewer incorporates techniques including render around a point and hybrid rendering (i.e., combined volume rendering, surface rendering, and multiplanar [MPR] display). These techniques are the subjects of previous U.S. Pat. Nos. 5,782,762 and 5,920,319, the disclosures of which are incorporated herein by reference. When surface rendering and MPR are utilized, identification of new diagnostically significant features, discussed below, within the 3D environment works in the same fashion, with a RMB click. When the 3D viewer is activated after a diagnostic finding has been created, the volume-rendered image, e.g., a cube of CT data, (or surface-rendered or MPR image(s)) is centered around the coordinates of the diagnostic finding.

A render-box-size menu is also provided in the user-interface to control the size of the volume (i.e., cube of digital data) rendered in the 3D viewer. When changing the volume size, the 3D display automatically adjusts the scene to fill the screen. An opacity-map menu, Op, in the 3D viewer permits the radiologist to control the level of transparency and grayscale/color scale of a 3D volume rendering. In addition, the opacity map function (or transparency) and grayscale/color map can be set by the system in response to the selection of an anatomical:pathological code by the radiologist, as described below. Furthermore, the system provides functions to manipulate the 3D object/scene including but not limited to zoom, cutting plane, and opaque cutting plane features.

As a further aspect of the display step 310, an orientation button is provided in the user-interface to allow the radiologist to properly set the orientation of the image data prior to 3D rendering. For example, it is assumed that the 2D first image in a CT series is the most superior (i.e., highest) image, the patient's left is on the radiologist's right, and the patient's anterior surface is facing up. If the series needs to be reoriented, the radiologist can pan through the collection of images to locate the most superior image (or close to it). The radiologist then toggles the orientation button, at which time the 2D viewer goes into an orientation mode. The radiologist freely rotates the image plane by pressing the LMB and moving the mouse until the proper anterior/posterior and left/right orientation is achieved. Finally, the radiologist toggles the orientation button again to set the proper orientation. The 3D viewer then automatically adjusts the image plane so that it is orthogonal to the radiologist's viewpoint. The 3D scene can also be automatically annotated with labeled 3D axes to assist in the visual orientation by the radiologist.

The volume-rendered image can be manipulated in various ways (i.e., using opacity maps, cutting planes, rotation, and fly-throughs). A second method for switching between the 2D and 3D viewers is to click on a 2D thumbnail image representation of a diagnostic finding (or its appended secondary 2D and 3D images) shown in an intermediate report display, thereby recalling the last state of the 2D or 3D viewer associated with the newly activated finding.

When transitioning between 2D and 3D viewers, the last state of each viewer is stored. For example, the proper grayscales (or color scales) and opacity maps are applied according to the last recalled W/L or Op settings, respectively. Similarly, when jumping to a previous finding by clicking on its thumbnail image representation, the last W/L and/or Op settings for that finding are recalled depending on whether the thumbnail represents a 2D or 3D image. A previous button, Pr, allows the radiologist to toggle between the two most recent W/L settings or Op settings in the 2D and 3D viewers, respectively. Alternatively, the user can press on the LMB followed by a click of the RMB to activate the Pr function.

Usually a radiologist compares a current examination to previous examinations by way of old reports and/or images. A conventional radiology report and images can be considered to represent unorganized sets or collections of diagnostic findings. Due to the database organization of diagnostic findings created by this invention, the system has the ability to aid in analysis of a current examination, by presenting, at step 311, the radiologist with an organized display of significant prior findings extracted from the previous reports retrieved by the file loader.

Figure 9A:
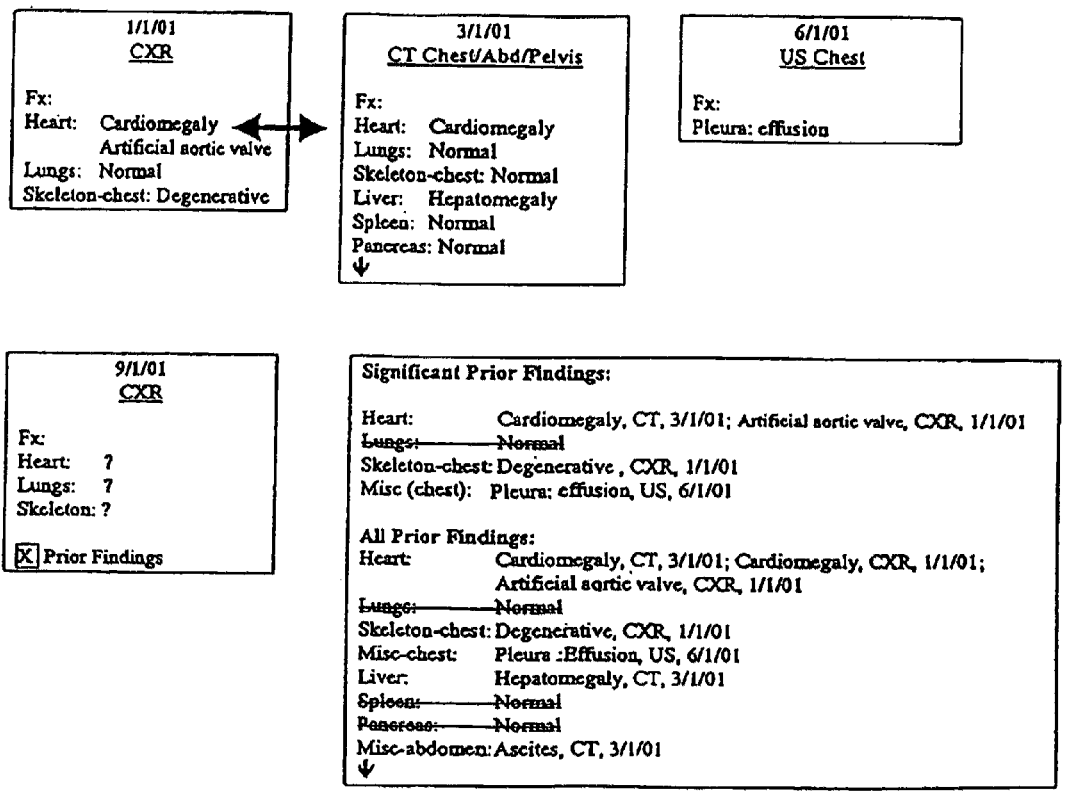
Figure 9B:
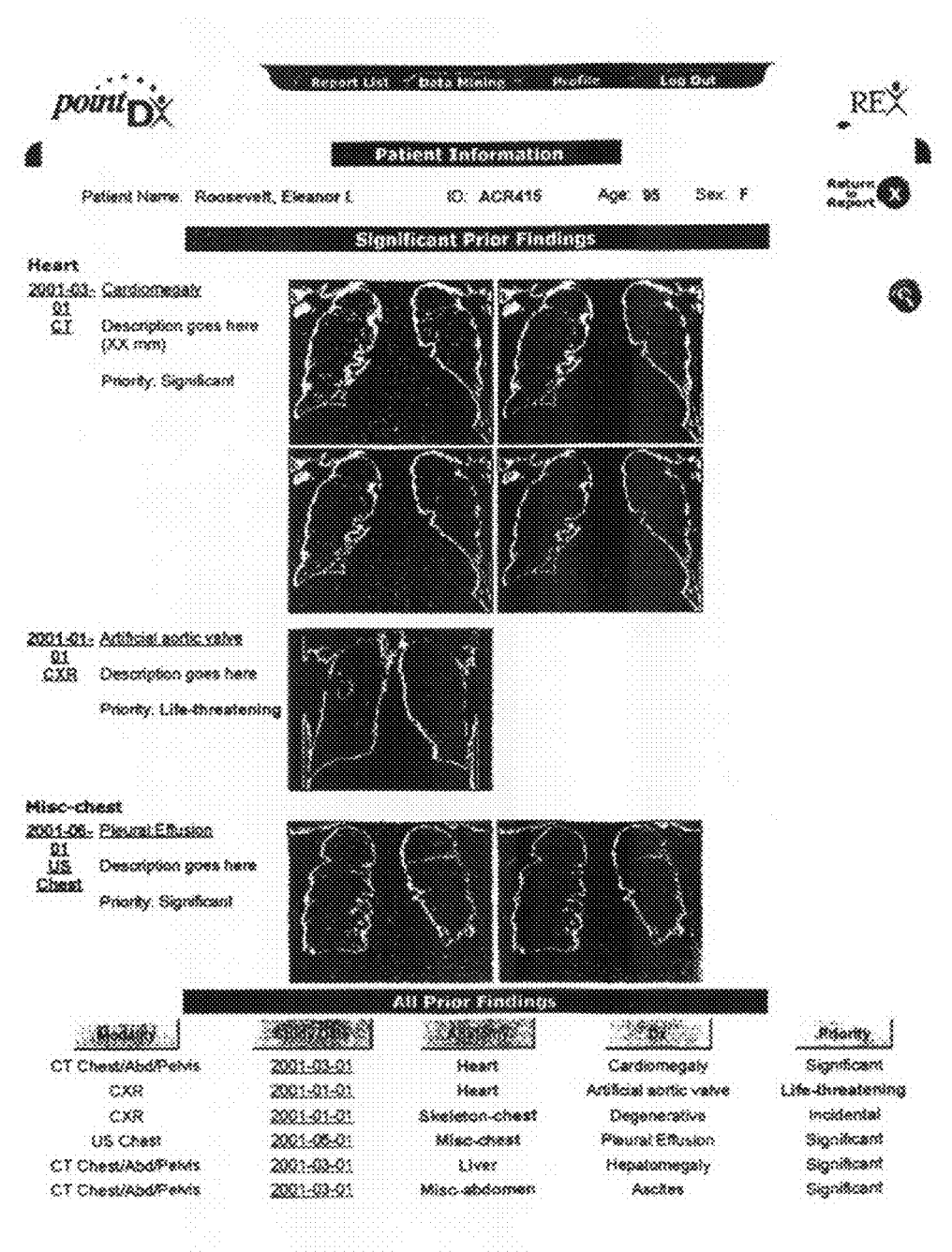
Figure 9C:
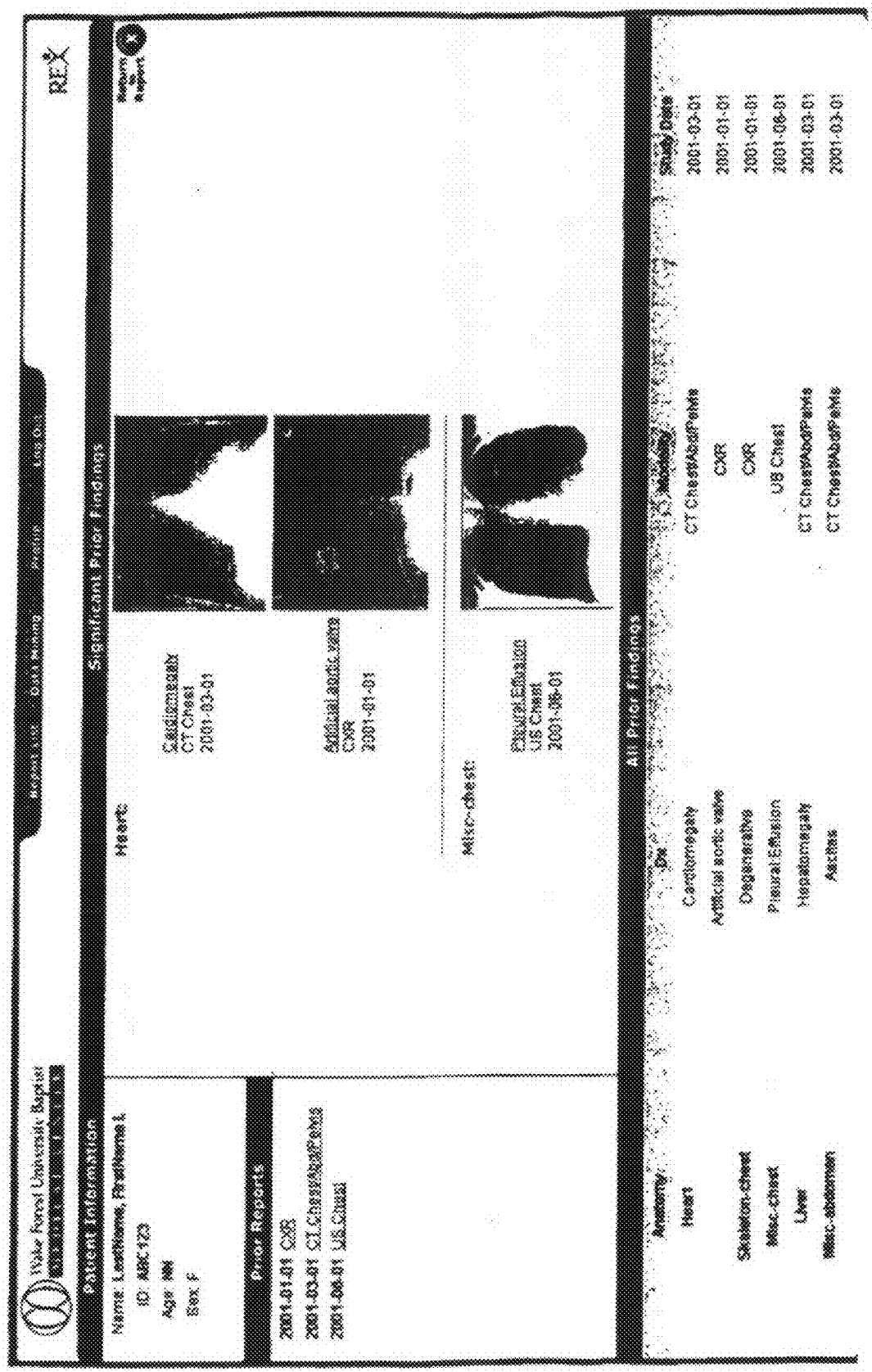
Figure 10:
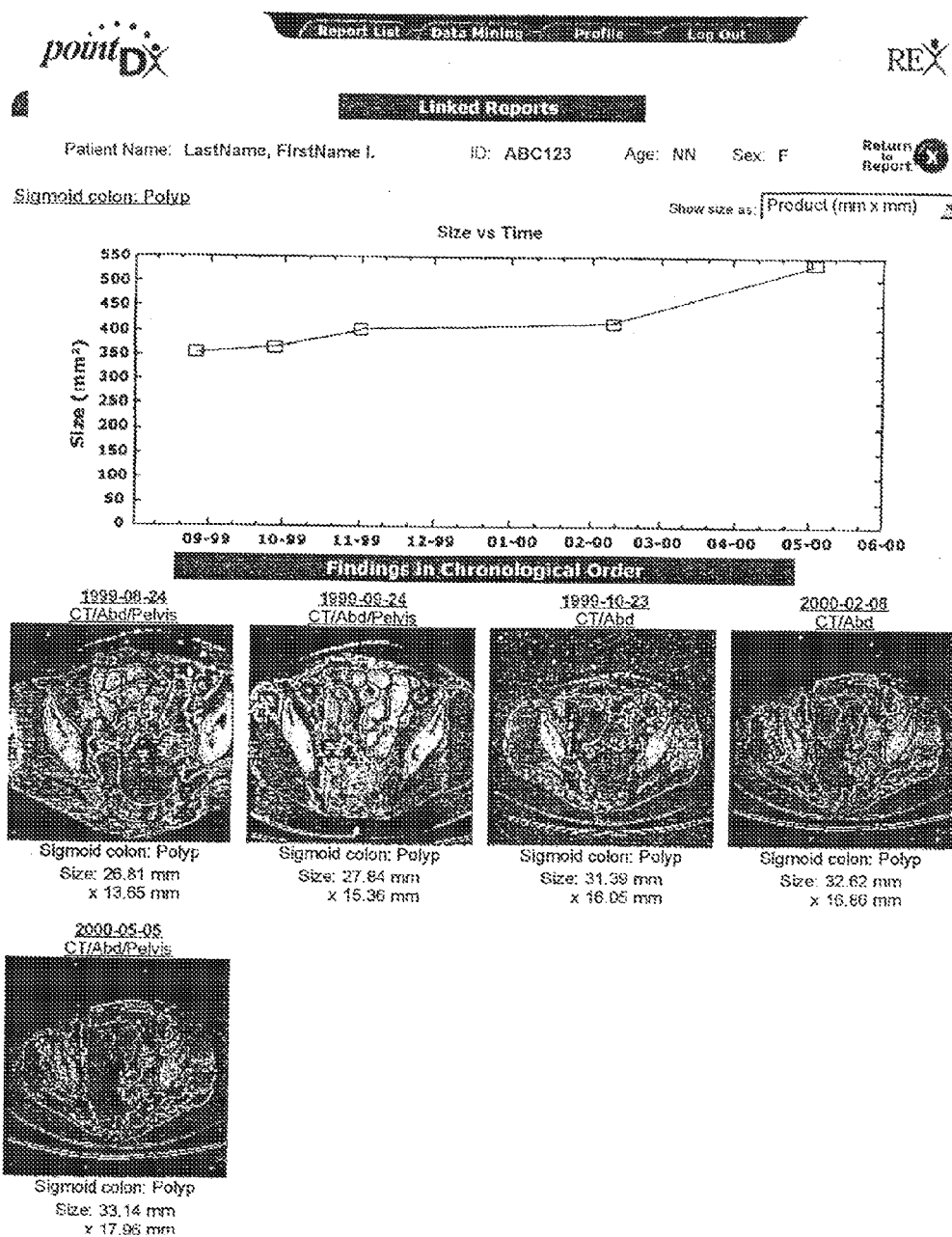
FIG. 10 illustrates a report showing the tracking of a disease.

As shown in FIG. 9A, the prior findings may be divided into "Significant Prior Findings" and "All Prior Findings", as shown in FIG. 9A. For example, the finding for the "Liver" shown in "All Prior Findings" section of the report does not appear in the "Significant Prior Findings" section of the report. This omission of the liver may be due to the fact that the "Liver" is unrelated to the "Heart," "Lung," or "Skeleton" of the 9/1/1 procedure or the CPT code for the 9/1/1 procedure. Another reason for the omission may be that the "Liver" finding was not designated with a sufficient level of significance. The prior findings may be sorted by a designated priority code, anatomy, or modality (e.g., x-ray). In addition, the presentation of prior findings may include stored images associated with the findings, as shown in FIGS. 9B and 9C. In the case where the prior findings are part of a horizontally linked series, described below, the radiologist may be presented with a trend report which shows a chronological tracking of a finding, such as tumor size, as shown in FIG. 10.

During review of an image using the viewers as described above, the radiologist searches for any diagnostically significant image features. When the radiologist locates a diagnostically significant feature, the radiologist begins the process of recording a diagnostic finding at steps 106 and 312. The process of recording a diagnostic finding begins with positioning the cursor over the location of the feature on the digital image and clicking the RMB at step 312. Alternatively, when applying the invention to conventional x-rays or images, a digital camera device can be pointed at an image finding, and a representative digital image can be recorded. Alternatively, the radiologist may point at the feature by using an intelligent view box. Clicking on the RMB stores the image coordinates, for example DICOM coordinates, and an image number corresponding to the cursor location in a database. To complete the definition of a diagnostic finding, an anatomical:pathological code and, optionally, secondary attributes are assigned to the image coordinates and automatically stored in the database. The anatomical code identifies the anatomical location within the body, and the pathological code describes the radiologic pathology of the identified image feature. The anatomical:pathological codes may be derived from a predefined lexicon, such as the American College of Radiology (ACR) Index of Radiological Diagnoses or Systematized Nomenclature of Medicine (SNOMED). The secondary attributes provide additional descriptions of the finding and include, for example distance, area and volume measurements, characteristics and status of the finding, as well as multimedia information such as audio descriptions, 3D snapshots, and 3D illustrated movies.

In response to the RMB click the reporting system can automatically display a pop-up anatomical-location menu at step 314. The anatomical-location menu may consist of a cascading list of anatomical location codes that have been customized based on the previously verified CPT and ICD codes; i.e., the anatomical-location menu presents only the anatomical organs associated with a particular radiologic examination. The cascading anatomical-location menu provides greater levels of detail of the finding's anatomical location with each cascading level presented. For example, a first level might specify "Colon", and a second level "Sigmoid Colon". Upon selection of an anatomical code, the reporting system displays a cascading pathology-code menu, at step 316, which displays a cascading list of pathology codes that correspond to the selected anatomical location. For example, a first level of the pathology-code menu might specify "Neoplasm", the second "Benign Neoplasm", and the third "Polyp". An anatomical:pathological code must be assigned to any unlabeled findings prior to final report approval; otherwise, these findings are labeled with the default "unknown location:unknown pathology" or any combination thereof. If no abnormal findings are entered for a particular anatomy (i.e., for anatomical organs contained within the scope of an examination described by a CPT code), then a "Normal" default may be applied as a summary diagnosis for that organ. When a diagnostic finding has an indeterminate etiology, the radiologist my assign a list of diagnostic possibilities, representing a differential diagnosis, as secondary attributes of that finding. Alternately, the reporting system 10 can incorporate voice activated control and natural language processing in conjunction with or instead of the pop-up annotation menus, i.e. the anatomical-location and pathological-description menus. The radiologist could speak "Sigmoid Colon Polyp" to achieve the same result as using the annotation menus.

As each diagnostic finding is created, a representative thumbnail image 620, as shown in FIG. 6, may be displayed on the right side of the 2D and 3D viewers for immediate presentation and recall, and the thumbnail images later may be incorporated into the final report. Alternately, the report with thumbnail images can be displayed on a second independent monitor as it is being created. The above method for entering an anatomical:pathological code is denoted "click and label". Two alternative methods are also possible for performing steps 314 and 316.

The first alternative method, "click-pause-label", allows the radiologist to postpone assignment of an anatomical: pathological code until sometime later during the analysis of the finding. In this case, the radiologist must deliberately press anatomy-location and/or pathology-description button, An and Pa, on the 2D or 3D viewer, as shown in FIG. 6, to subsequently activate the corresponding pull-down (as opposed to pop-up menu) annotation menu. The second alternative method, "click-click-click and label-label-label", allows the radiologist to annotate the diagnostic findings during final report editing. A more detailed description of these two methods is discussed below in conjunction with the method of operation of the reporting system.

The method of entering and annotating diagnostic findings is not limited to computer pop-up and pull-down menus containing preselected terminology. Keyboard, voice recognition, macros, and natural language processing are available to enter diagnostic findings and secondary attributes.

After assignment of the anatomical:pathological codes, secondary attributes may added at step 318 to embellish or support the diagnosis. As shown in FIG. 6, the user-interface 600 of the reporting system 10 includes various options for adding secondary attributes. A chart of the symbols used on FIG. 6 are set forth in the following chart. The options may be available in one or more of three major subsystems of the invention, as shown in the third column of the chart. The three major subsystems include image analysis (IA), report generation (RG), and report viewing (RV). The image analysis subsystem includes the image loading, step 100, and a display of the images, step 104. The report generation subsystem includes the recording of the findings, step 106, annotation of findings, step 108, and creation of links/groups, step 110. The report review function includes algorithms associated with step 112.

| An | Annotation menu listing ACR Dx codes | RG |
|---|---|---|
| Vo | Volume measurement button | IA |
| Ch | Characteristic button | RG |
| Di | Distance measurement button | IA |
| Ar | Area measurement button | IA |
| Au | Audio record button | RG |
| Pt | Priority button | RG |
| Rm | Recommendation button | RG |
| Sn | Snapshot button | IA & RG |
| Mo | Movie button | IA & RG |
| W/L | Window/Level presets menu | IA |
| | Orientation button | IA |
| | Overview button | IA |
| Pr | Previous window/level setting toggle button | IA |
| 2D/3D | 2D/3D viewer toggle button | IA |
| Cr | Cursor on/off toggle button | IA |
| Series | Series menu | IA |
| MPR | Multi-planar button | IA |
| Surf | Surface rendering button | IA |
| Op | Opacity map presets menu | IA |
| 64 | Render box size menu | IA |
| ■ | Opaque cutting plane toggle button | IA |

For example, a characteristics button, Ch, is included to activate a menu of descriptive attributes that enhance a specific diagnostic code set, (i.e., anatomy:pathology code combination). For example, "liver:metastatic neoplasm from colon" (ACR diagnostic code 761.3375) can be further characterized with the number of lesions (i.e., single or multiple).

A distance-measurement button, Di, is included in the user-interface of the reporting system 10 to permit the radiologist to measure a finding in the 2D or 3D viewer with any number of diameters. Similarly, an area-measurement button, Ar, allows the radiologist to define a region-of-interest (ROI) from which the cross-sectional area, mean pixel or voxel value (depending on whether the measurement is made on a 2D or 3D image, respectively), and standard deviation of pixel or voxel values in that region can be calculated. Measurements automatically become secondary attributes of the active diagnostic finding and are stored in the database associated with the diagnostic finding. Additionally, a volume-measurement button, Vo, is provided to permit the radiologist to define a volume-of-interest VOI. The reporting system 10 can create the VOI by 3D segmentation means, as disclosed in U.S. Pat. Nos. 5,782,762, 5,920,319, and 6,083,162, each of which are incorporated herein by reference. A volume measurement calculated from the VOI may be added as a secondary attribute.

The reporting system also permits the assignment of both priority levels and recommendations to a finding. A priority button, Pt, permits the radiologist to add a certain level of significance to a diagnostic finding at step 319. For example, the priority level may be selected from a predefined list containing entries such as "(1) Life-Threatening", "(2) Significant", "(3) Index", "(4) Repetitive", and "(5) Incidental", and such entries may be presented as part of any subsequent report, as shown in FIG. 9B. One of more of priority levels may be combined, such as "Life-Threatening" and "Index". An "Index" priority denotes a trackable finding, as described below. The priority level can also be used to generate the production of the "Significant Prior Findings" and "All Prior Findings" as shown in FIG. 9A. For example, the "Significant Findings" may include prior findings designated with a priority of level of "Life-Threatening" or "Significant." Hence a selected priority level or set of levels can be used to select the findings for inclusion as "Significant Prior Findings" in the report of FIG. 9A. A recommendation button, Rm, can be used to label a "Sigmoid Colon: Polyp" diagnostic code with a recommendation such as "Recommend colonoscopy for polyp removal." By default, the reporting system 10 does not assign any particular priority or recommendation to a diagnostic finding; however, certain diagnostic codes may be assigned default priority and recommendation codes which may be changed by the radiologist.

An audio button, Au, is included in the user-interface to allow the radiologist to dictate a verbal description of a diagnostic finding, and that audio file becomes a secondary attribute of the finding. The audio file can be saved in the final report unchanged, or it can be transcribed to text by a typist or a voice recognition system.

A snapshot button, Sn, in the user-interface allows the radiologist to record any number of additional 2D and 3D images as secondary attributes of a diagnostic finding. For example, a "colon:polyp" diagnostic finding could be supported by additional 3D snapshots of the polyp. In the case of "spine:arthritis" which is seen over a large portion of the skeleton, a single diagnostic finding can be created to establish the diagnosis, and additional snapshots of other sites of the disease can support the diagnosis. Alternatively, creating multiple individual diagnostic findings documenting arthritis could achieve the same result. Additionally, the recording system provides the ability to place a marking symbol in the 2D or 3D images indicating the location of the selected feature. The snapshot function also records the location of the marking symbol visible within the 2D or 3D viewer, as well as the state of the 2D or 3D viewer at which time the Sn button was pressed.

A movie button, Mo, functions in a similar manner by appending cine clips of moving 2D or 3D images, including active annotations and voice descriptions. The active annotations can take the form of freehand notations "drawn" over the 2D or 3D images during recording of the cine clip. The drawn freehand notations can be similar to "chalkboard-style" markings used by television commentators to diagram and analyze football plays.

To assist radiologists in establishing a diagnosis, the annotation menus may also provide links to reference materials and example images related to each potential diagnostic code set combination. The annotation menus may include options to undo accidental RMB clicks. The reporting system 10 also permits the radiologist to recall the annotation menus to reassign a diagnostic code to a particular finding if the diagnosis is revised during the evaluation process.

The reporting system 10 may also perform computerized diagnoses at step 320. For example, computer-assisted polyp detection (CAPD), as disclosed in U.S. Pat. No. 5,920,319, can be integrated with the system so that CAPD-identified polyps can be automatically correlated with radiologist-defined polyps by correlating the proximity (i.e., Euclidean distances) of image finding coordinates. The identified diagnostic findings can be used to support advanced applications, such as the creation of "polyp maps" for subsequent endoscopic or surgical guidance. A polyp map consists of a 3D-rendered colon with highlighted polyp locations.

Another example of an advanced application that this reporting system supports is a Transbronchial Needle Aspiration (TBNA) targeting scheme. The TBNA application uses the stored data in the reporting system 10 to automatically construct airway models and lymph node targets (i.e., surface-rendered models of the anatomy generated using the respective finding coordinates). TBNA is a bronchoscopy technique that permits a needle biopsy of suspicious mediastinal lymph nodes. The tracheobronchial tree and lymph nodes are defined by their diagnostic finding coordinates, respectively, and are assigned secondary attributes by the radiologist to indicate the TBNA lymph nodes as targets. Further refinement of the lymph node targets (i.e., modeling lymph nodes as spherical or ellipsoid objects) can use the distance, area, and volume measurements that are generated as secondary attributes of those lymph nodes.

After the review of the image(s) is deemed complete, the report display is presented for the radiologist to review at step 332. The report display is invoked by pressing a report button in the user-interface to activate the report display. Alternately, when using a two-monitor system or a wide monitor display, the report can be shown simultaneously as it is being generated. The reporting system 10 sorts the diagnostic findings according to anatomical categories, with high priority findings placed at the top of each category. The reporting system 10 can also order the findings by priority levels, irrespective of anatomical categories, or by chronology, indicating the order in which the findings were recorded by the radiologist. The reporting system 10 highlights each high-priority finding (e.g., life-threatening and significant findings, levels 1 & 2) with color-enhanced text. The radiologist edits the final report as necessary, including linking redundant findings at step 324.

A powerful feature of the paradigm's report format and database structure is the ability to link and track diagnostic findings within the same examination (i.e., vertical linking) and across serial examinations (i.e., horizontal linking). For example, a CT examination generally consists of a hierarchy of series/acquisitions/images. A diagnostic finding identified on an image within one series may also be seen in another series of the same examination. The reporting system 10 provides the ability to vertically link (group or combine) such diagnostic findings within its database. In one implementation, the radiologist "drags and drops" a finding onto a matching finding in the report display to achieve linking, and the "dropped" finding becomes a subset of the primary finding. Alternatively, the reporting system 10 could perform linking via a command-line interface, voice-activated control, or graphical interface, i.e., highlight user-selected related findings and press a "Group" button. The purpose of vertical linking is to manage redundancy of report information.

Similarly, the reporting system 10 provides horizontal linking as a means to track and monitor a diagnostic finding over time and across various imaging modalities. In horizontal linking, diagnostic findings can be "dragged and dropped" across reports. In this case, the diagnostic findings exist independently in their respective reports and do not necessarily become subsets of other findings. Horizontal linking provides a means to efficiently analyze a particular diagnostic finding over time (i.e., disease tracking). As illustrated in the report of FIG. 10, the size of a tumor can be automatically presented in graphical format as size versus time. The size of the tumor can be selectively measured as an axial distance, area, volume, or other function.

An extension of "linking" is "compositing." A group of image findings (e.g., pleura:pleural effusion, heart:cardiomegaly, lung:pulmonary edema) can be composited (i.e., linked or grouped) by the radiologist or by an artificial intelligence (AI) program to yield a cumulative diagnosis of "congestive heart failure." Similarly, the radiologist or an AI program can composite other clinical information (e.g., laboratory values or pathology reports) to support and establish a diagnosis. For example, specific findings may be grouped by use of a "Group" button followed by selection of specific annotations to describe the grouped set of findings.

The reporting system 10 also allows for the automatic incorporation of repetitive findings (i.e., designated as a "Repetitive finding" using the above priority assignment feature) from previous reports into a new report (e.g., evidence of prior gallbladder surgery). If a previous report contains a "trackable" finding (i.e., designated as an "Index finding"

using the above priority assignment feature), that previous finding is brought to the attention of the radiologist. In this case, the trackable finding can be linked horizontally across reports, and the temporal progression of this finding, as shown in FIG. 10, can be observed in a specialized viewer.

The report display also includes a suspend-resume button for suspending or resuming an examination in case the radiologist is interrupted during the review. Upon completion of the report, the reporting system 10 stores and sends the final report, as shown in FIGS. 7A-C, at step 326. The reporting system 10 may issue the report by any combination of telephone, fax, pager, e-mail, or wireless PDA and may include return receipt verification. The automated sending and receipt verification allows the radiologist to quickly communicate his or her findings and track this communication. Along with the prioritized and highlighted presentation of the most significant findings, the automated sending feature of the reporting system 10 helps to fulfill the radiologist's duty for timely communication of results and follow-up on the findings.

The reporting system also supports "real-time dynamic radiology." Each diagnostic finding is annotated with a timestamp. After an initial report is "signed off," any future changes to the report can be recorded as a history of the report. Any subsequent significant changes can be automatically communicated to a clinician and verified upon their receipt.

The reporting system 10 monitors how the radiologist reviews an examination. The final report can also indicate how much time a radiologist spends reviewing an exam, number of findings, and average time per finding. Statistics, including total review time, time per finding, number of findings, and diagnostic accuracy, are compiled during a review session and are reported as needed. This feature creates a utilization management and quality assurance measure that is appealing to the Health Care Financing Administration (HCFA) and health maintenance organizations (HMOs). In addition, physician profiling may be employed for utilization management to review the ordering practices of referring physicians.

The final report can also be automatically translated into a foreign language using the standardized lexicon of anatomical:pathological codes and simple lookup tables.

Healthcare organizations further benefit from the automation and efficiency of the system. In particular, billing speed and accuracy are increased. Billing requires matching of ICD and CPT codes, a task that currently requires highly-trained personnel to decipher radiology reports and verify proper code assignments. Incorrect coding results in denied or delayed reimbursement by insurers. However, the present reporting system automates the process and allows radiologists to approve the coding process.

Figure 4:
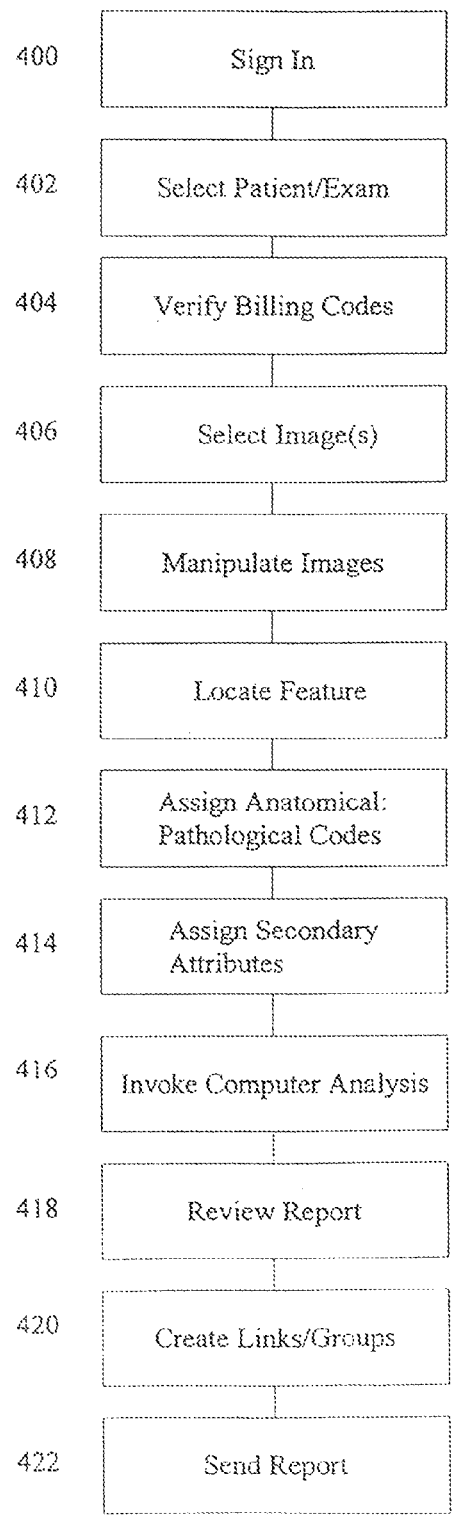
FIG. 4 illustrates a flowchart representing steps of operation of the method of the present invention.

The method of operation is best illustrated by its application in the field of radiology as shown in FIG. 4. Upon starting the software program, the radiologist signs in, with either a password or voice signature or any other security measure, to begin the evaluation at step 400. Secure sign-in protects access to the database and validates the identity of the radiologist generating the report. The file loader displays a work list of patients whose examination studies are accessible. The radiologist selects the name of a patient at step 402, and the file loader displays all of the associated unread examination files. The radiologist selects a particular examination file, and that examination file is loaded into computer memory.

The file loader displays the CPT and ICD codes assigned to a particular examination. This information can be obtained from the HIS 36 or entered manually. The radiologist verifies the CPT and ICD codes and makes any necessary changes at step 404. Correct assignment of the CPT and ICD codes by the radiologist is essential for electronic billing and expedited reimbursement by insurers.

After validation of the CPT and ICD codes, the radiologist begins analysis of the first image presented in the 2D viewer or selects an alternate image, at step 406, from the series menu which lists all of the images or sets of images (i.e., series) in a patient exam available for review. The radiologist may change the displayed image in order to locate diagnostically significant features in other images at step 408. For example, the radiologist may press the LMB while moving the mouse to pan through multiple images in the 2D viewer (provided that more than one image is contained in the series). The radiologist may also translate the displayed image up, down, and sideways by pressing the MMB while moving the mouse. The radiologist may also zoom the displayed image by pressing the LMB and MMB simultaneously while moving the mouse. In the 3D viewer, the mouse operations are similar except that pressing the LMB while moving the mouse causes the 3D rendered scene to rotate in space or to guide a "flythrough." Alternatively, multiple images or series can be displayed simultaneously in separate windows in the image analysis (IA) viewer.

To aid in the identification of diagnostically significant features, the radiologist may toggle between 2D and 3D viewers by pressing the 2D/3D toggle button as shown in FIG. 6. When the 3D viewer is initially activated, a volume-rendered image centered around the coordinates of the identified feature is created (i.e., a cube of CT data is volume-rendered). The radiologist may adjust the size of the volume (i.e., cube of digital data) that is rendered in the 3D viewer via the render-box-size menu. The radiologist may further adjust the volume-rendered image in various ways, such as using opacity maps, cut planes, and rotation. MPR and surface rendering can also be activated in the 3D viewer.

When the radiologist toggles between 2D and 3D viewers, the last state of each viewer is recalled. The radiologist may also toggle between the 3D and 2D viewers by clicking on a primary 2D thumbnail image representation of a diagnostic finding (or its supporting secondary 2D and 3D thumbnails), thereby recalling the last state of the 2D or 3D viewer associated with the activated finding. The cursor position and location of any marking symbols in the display are recalled as part of the last state of the viewer. The 2D or 3D viewer then enters an edit mode, during which the radiologist can append additional secondary attributes to the activated diagnostic finding, and these are subsequently stored in proper locations within the database.

The radiologist can also set the orientation of the image data prior to image analysis. If an image or image series needs to be reoriented, the radiologist pans through the volume of images to locate the most superior image (or close to it). Then, the radiologist toggles the orientation button, at which time the viewer goes into an orientation mode. The radiologist rotates the image plane by pressing the LMB and moving the mouse until the proper anterior/posterior and left/right orientation is achieved. Finally, the radiologist toggles the orientation button again to set the proper orientation. The viewer automatically adjusts the 2D image plane so that it is orthogonal to the radiologist's viewpoint.

The radiologist has further control over the display of the images such as W/L (i.e., grayscale or color scale) and 3D opacity maps settings. The radiologist may toggle between the two most recent W/L settings or Op settings in the 2D and 3D viewers by pressing the previous button, Pr, as shown in FIG. 6, or simultaneously pressing the LMB and RMB. Additionally, the radiologist may toggle a visible cursor on and off by pressing a cursor-toggle button, Cr, as shown in FIG. 6, to indicate the location of a finding in both the 2D and 3D viewers. By pressing the overview button, the radiologist re-centers a 2D or 3D volume-rendered image in case the scene is moved out of sight.

When the radiologist locates a diagnostically significant feature, the radiologist positions the cursor over the location of the feature on the digital image and clicks the RMB to mark the feature at step 410. Clicking on the RMB stores the image coordinates and image number corresponding to the cursor location in database. To complete the definition of a diagnostic finding, the radiologist annotates the point (location) by assigning an anatomical:pathological code and optionally assigning secondary attributes at steps 412 and 414. This annotation is stored in the database, and it may also be displayed as a text overlay on the image.

The radiologist selects an anatomical:pathological code from a predefined lexicon, such as the ACR Index of Radiological Diagnoses or SNOMED or a custom designed lexicon, to create a diagnostic finding. As each diagnostic finding is created, a representative thumbnail image 620 may be displayed on the right side of the 2D and 3D viewers, or in a separate display, for immediate review and recall, and the thumbnail images later may be incorporated into the final report as shown in FIGS. 7B and 7C.

The radiologist enters the anatomical:pathological code by one of several modes. In a first mode, "click and label", cascading pop-up annotation menus are presented to the radiologist immediately after a feature is marked by an RMB click at step 500 of FIG. 5A. The radiologist selects an appropriate anatomical location description from the anatomical-location menu at step 502. For example, the radiologist may select Colon: Sigmoid colon. After the selection, the radiologist selects the pathological description from the pathology-description menu at step 502. For example, the radiologist may select Neoplasm:Benign Neoplasm:Polyp. A secondary attribute may then be assigned at step 504.

In a second mode, "click-click-click and label-label-label", the radiologist identifies all the diagnostically significant features first and subsequently annotates the features with diagnostic codes and secondary attributes. As shown in FIG. 5B, the radiologist marks a designated feature at step 550 and then proceeds to mark successive features by repeating step 550. After all desired features are marked, the radiologist assigns a diagnostic code to each marked feature by assigning an anatomical code at step 552 and a pathological code at step 554. Secondary attributes are assigned at step 556 either following the marking of a feature at step 550 or the assigning of anatomical and pathological codes at steps 552 and 554. The radiologist must assign a diagnostic code to any unlabeled findings prior to final report approval; otherwise, these findings may be labeled with a default "Unknown Location: Unknown Pathology." Additionally, the radiologist may recall the annotation menus to reassign an anatomical:pathological code to a particular finding if the diagnosis needs to be revised during the evaluation process.

The radiologist may also assign secondary attributes to embellish or support a diagnostic finding at step 414, but secondary attributes are not required for establishing a diagnostic finding. The radiologist may enter descriptive characteristics, dimensional measurements, audio descriptions, and specific snapshots of particular views of the identified finding as secondary attributes. For example, the radiologist may add descriptive characteristics that enhance a specific diagnostic code set from a characteristics menu of descriptive characteristics.

The radiologist may measure one or more dimensions of a finding, for example, a diameter of an identified feature in the 2D or 3D image. The radiologist activates the distance measuring function by pressing the distance-measurement button, Di, as shown in FIG. 6. The radiologist measures the distance by clicking on first and second object points which span the characteristic length. Similarly, the radiologist may measure the area of an identified feature by pressing the area-measurement button, Ar, as shown in FIG. 6 and defining a region-of-interest (ROI) using the input device 27. The cross-sectional area, mean pixel or voxel value, and standard deviation of pixel or voxel values in the ROI can be calculated. The radiologist may also add a volume-measurement as a secondary attribute by pressing the volume-measurement button, Vo, as shown in FIG. 6.

As part of step 414, the radiologist may also add a priority level and recommendation to the diagnostic finding by pressing the priority button, Pt, or recommendation button, Rm, respectively, as shown in FIG. 6. In addition, the radiologist may append a verbal description of the diagnostic finding in the form of an audio file. To add a verbal description the radiologist presses the audio button, Au, as shown in FIG. 6 to initiate recording and then dictates a verbal description of the diagnostic finding. The radiologist presses the audio button again to stop recording, and an audio file of the verbal description is stored in the database attached to the finding. Audio files can be attached to "grouped or linked" findings or attached to individual snapshot images or movies. Audio files may be edited and/or appended with additional audio clips.

Additionally, the radiologist may record snapshots of any of the displayed 2D and 3D images as a secondary attribute by pressing the snapshot button, Sn, as shown in FIG. 6. For example, the radiologist may record any number of additional images showing differing views of a particular diagnostically significant feature. For example, a "colon:polyp" diagnostic finding could be supported by additional 3D snapshots of the polyp. The radiologist may also append cine clips of moving 2D or 3D images (including audio and active annotations) as a secondary attributes in a manner similar to recording snapshots by pressing the movie button, Mo, as shown in FIG. 6. Pressing of the movie button starts and stops the recording of the cine clip.

Prior to final report review, the radiologist may also invoke computer-aided location and analysis of diagnostically significant features, at step 416, whereby the system automatically identifies and diagnoses suspicious image features. For example, the radiologist can review polyps found by the CAPD that were not previously identified by the radiologist.

After the radiologist's review is deemed complete, the radiologist clicks a report button on the bottom of either the 2D or 3D viewer as shown in FIG. 6 to activate the report display at step 418. Alternately, the report can be generated and simultaneously displayed on a second monitor while the diagnostically significant findings are being located and annotated. The diagnostic findings are sorted according to anatomical categories and priorities, with high priority findings being placed at the top of each category. Each high-priority finding is highlighted with color-enhanced text. The sorting and highlighting of the diagnostic findings alerts the end-user to the most significant diagnostic findings. Alternatively, the findings may be sorted by chronological order.

The radiologist edits the final report as necessary, including linking redundant findings at step 420. This process could also be automated with artificial intelligence and detaining algorithms. The step of creating links, step 420, may be performed before or after the step of reviewing the report, step 418, as depicted in FIG. 1, where the step of creating the links, step 110, occurs prior to the step of reviewing the report, step 112. In one implementation of vertical linking, the radiologist "drags and drops" a finding onto a matching finding in the same report display, and the "dropped" finding becomes a subset of the primary finding. Alternatively, the radiologist can form links via a command-line interface or voice-activated commands (control). Similarly, the radiologist may assign horizontal linking to track and monitor a diagnostic finding over time and across various imaging modalities (i.e., disease tracking). In horizontal linking, diagnostic findings can be "dragged and dropped" across reports in a similar fashion.

The radiologist may also composite a group of image findings to yield a diagnosis as illustrated above for "congestive heart failure." In this process, the radiologist or an AI program can link/group/composite additional clinical information (e.g., laboratory and pathology report values) to support a diagnosis.

The radiologist further reviews any repetitive diagnostic findings from previous reports which are brought to the attention of the radiologist by the system. If a previous report contains a repetitive diagnostic finding (e.g., evidence of prior gallbladder surgery), that finding is presented to the radiologist for automatic incorporation into the new report. If a previous report contains a "trackable" diagnostic finding (e.g., index lymph node measurement), the radiologist can link the trackable diagnostic findings horizontally across reports, and the temporal progression of this diagnostic finding can be observed in a specialized viewer.

The radiologist can suspend an examination for later resumption by pressing the suspend-resume button during the review. Upon completion of the report the radiologist instructs the system to send the report to the end-users (e.g., clinicians) at step 422. Additionally, the end-user can access the report via a Web server after the report has been posted. As noted above, the report may be sent by a combination of telephone, fax, pager, e-mail, or wireless PDA and may include return receipt verification. The automated sending and receipt verification allows the radiologist to quickly communicate his or her findings and verify this communication.

End-users receiving the radiologist's report can customize the display of the information to best suit their needs. For example, when the reporting system is integrated with a PACS and/or HIS system, the clinician can click on a thumbnail image in the final report to access the original PACS or HIS image data. For convenience the PAC or HIS image data may be displayed on one screen or display terminal while the report data is displayed on a separate screen or display terminal. Additionally, the reporting system can automatically translate the radiologist's report into a different language for the end-user. The standardized lexicon of diagnostic findings supports rapid translation of reports to foreign languages by employing translation look-up tables.

The reporting system of the present invention has further application beyond the preparation and delivery of reports. The ability of the reporting system to enter diagnostic findings into searchable databases readily supports data mining for clinical trials, epidemiology studies, and outcomes analyses.

Additionally, the reporting paradigm supports radiologic training. For example, a radiology resident can issue a preliminary report indicating his or her findings, and the preliminary report can later be modified by an attending radiologist to indicate any corrections. In the latter case, the system automatically informs the referring clinician of any significant changes. The history of report changes can be recorded with each finding (or changed finding) having a timestamp.

The reporting scheme also supports standardized testing (e.g., replacement of the American Board of Radiology's Oral Board examination) by objectively measuring a student's performance. Such an objective performance measure could also assist in comparing a radiologist's performance to that of a non-radiologist.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, while the above invention has been illustrated in terms of its application to the field of radiology, the invention is equally applicable to other fields of medicine as well as other image analysis fields such as satellite imagery and photography. It should therefore be understood that this invention is not limited to the particular embodiments described herein, but is intended to include all changes and modifications that are within the scope and spirit of the invention as set forth in the claims.

What is claimed is:

1. A computer program product, comprising a non-transitory computer usable medium having a computer readable program code embodied therein, the computer readable program code adapted to be executed to implement a method for analysis of an image from a series of images formed in a radiological examination of a subject comprising the steps of:
   a. retrieving image data comprising the image and an examination-code assigned to the radiological examination identifying the type of radiological examination,
   b. presenting the image to a user for analysis, to select and identify a feature of interest therein,
   c. receiving an identification of the selected feature from an input device to selectively mark a location on the image representing the selected feature,
   d. recording image coordinates of the selected feature within the image,
   e. generating a list of description-codes and a list of location-codes and a series menu using the examination-code,
   f. presenting the list of description-codes and the list of location-codes and the series menu to the user, the series menu listing the images or series of images formed in the radiological examination which are available for review by the user,
   g. receiving a description-code associated with the selected feature to describe an attribute of the feature, the description-code being selected by the user from the list of description-codes,
   h. receiving a location-code which describes the location of the selected feature within an object depicted in the image, the location-code being selected by the user from the list of location-codes, and
   i. creating an image finding of the selected feature comprising the recorded coordinates, the selected location-code and the selected description-code.

2. A computer program product according to claim 1, the computer readable program code adapted to be executed to implement a method for analysis of an image from a series of images formed in a radiological examination of a subject, comprising retrieving a prior report containing a most recent description code, and initializing a menu in response to the most recent description code to present menu items associated with the most recent description code first in the initialized menu.

3. A computer program product according to claim 1, the computer readable program code adapted to be executed to implement a method for analysis of an image from a series of images formed in a radiological examination of a subject, comprising retrieving a selected patient characteristic associated with the image, and initializing a menu in response to the patient characteristic to present items associated with the patient characteristic first in the initialized menu.

4. A computer program product according to claim 1, the computer readable program code adapted to be executed to implement a method for analysis of an image from a series of images formed in a radiological examination of a subject, comprising retrieving a plurality of prior findings of the selected feature from at least one prior analysis of an image, and displaying an element of the prior findings in a graphical display to describe a chronology of the element.

5. A computer program product according to claim 4, the computer readable program code adapted to executed to implement a method for analysis of an image from a series of images formed in a radiological examination of a subject, wherein the element comprises at least one of an area, volume, and a size of the selected feature.

* * * * *